(12) United States Patent
Gicquel et al.

(10) Patent No.: US 7,097,981 B1
(45) Date of Patent: Aug. 29, 2006

(54) REACTION WELLS, ASSEMBLY THEREOF, IMMUNOASSAY APPARATUS AND METHOD USING SUCH WELL ASSEMBLIES

(75) Inventors: Thierry Gicquel, Courdimanche (FR); Edouard Lentwojt, Saint-Leu d'Esserent (FR)

(73) Assignee: Biomerieux (FR)

( * ) Notice: Subject to any disclaimer, the term of this patent is extended or adjusted under 35 U.S.C. 154(b) by 0 days.

(21) Appl. No.: 09/554,167

(22) PCT Filed: Sep. 13, 1999

(86) PCT No.: PCT/FR99/02170

§ 371 (c)(1),
(2), (4) Date: Jul. 11, 2000

(87) PCT Pub. No.: WO00/16075

PCT Pub. Date: Mar. 23, 2000

(30) Foreign Application Priority Data

Sep. 11, 1998 (FR) .......................... 98 11375

(51) Int. Cl.
*G01N 33/53* (2006.01)
*G01N 35/00* (2006.01)
*G01N 21/75* (2006.01)
*G01N 33/36* (2006.01)
*C12M 1/00* (2006.01)

(52) U.S. Cl. .............. 435/7.1; 435/7.9; 435/283.1; 435/286.1; 435/286.2; 435/286.3; 435/286.4; 435/286.5; 435/286.6; 435/286.7; 435/287.1; 435/287.3; 435/288.7; 436/43; 436/47; 436/48; 436/49; 436/164; 436/165; 436/172; 436/807; 436/808; 422/62; 422/63; 422/64; 422/65; 422/66; 422/67; 422/68.1; 422/82.05; 422/82.07; 422/82.08; 356/246

(58) Field of Classification Search .......... 356/246; 422/62, 63, 64, 65, 66, 67, 68.1, 82.05, 82.07, 422/82.08; 435/7.1, 7.9, 283.1, 286.1–286.7, 435/287.1, 287.3, 288.7; 436/43, 47, 48, 436/49, 164, 165, 172, 807, 808
See application file for complete search history.

(56) References Cited

U.S. PATENT DOCUMENTS 3,865,495 A  *  2/1975  Sanz et al. .................. 356/246

(Continued)

FOREIGN PATENT DOCUMENTS

| EP | 0 837 331 | | 4/1998 |
|----|-----------|---|--------|
| JP | 05157699 | | 6/1993 |
| WO | WO 91/07662 | * | 5/1991 |
| WO | WO 96/14582 | * | 5/1996 |

*Primary Examiner*—Long V. Le
*Assistant Examiner*—Jacqueline DiRamio
(74) *Attorney, Agent, or Firm*—Michael Best & Friedrich LLP (57) ABSTRACT

The present invention relates mainly to reaction vessels, to sets of such vessels for automatic immunological assay apparatuses, to automatic immunological assay apparatuses making use of such sets of vessels, and to a method implementing sets of such vessels. According to the present invention, photometric detection is implemented of the luminescence of a reaction mixture found in a reaction vessel, the apparatus and/or the vessel guaranteeing light-tightness so as to prevent entry of external light falsifying the measurement. Advantageously, sets of vessels in accordance with the present invention are made out of a material that is opaque. The present invention is particularly applicable to detecting the presence of a chemical or a biological substance in a sample. The present invention applies mainly to medical analysis and research.

13 Claims, 4 Drawing Sheets

U.S. PATENT DOCUMENTS

| | | | | |
|---|---|---|---|---|
| 3,883,308 A | * | 5/1975 | Matte | 23/259 |
| 4,234,540 A | * | 11/1980 | Ginsberg et al. | 422/64 |
| 4,313,735 A | * | 2/1982 | Yamashita et al. | 23/230 R |
| 4,672,039 A | * | 6/1987 | Lundblom | 435/291 |
| 4,774,055 A | * | 9/1988 | Wakatake et al. | 422/64 |
| 4,818,883 A | * | 4/1989 | Anderson et al. | 250/361 C |
| 4,879,097 A | * | 11/1989 | Whitehead et al. | 422/67 |
| 5,048,957 A | * | 9/1991 | Berthold et al. | 356/246 |
| 5,073,029 A | * | 12/1991 | Eberly et al. | 356/432 |
| 5,380,487 A | * | 1/1995 | Choperena et al. | 422/63 |
| 5,397,539 A | * | 3/1995 | Hayashi et al. | 422/65 |
| 5,478,750 A | * | 12/1995 | Bernstein et al. | 436/164 |
| 5,482,839 A | | 1/1996 | Ashihara et al. | |
| 5,514,330 A | * | 5/1996 | Uzan et al. | 422/64 |
| 5,637,874 A | * | 6/1997 | Honzawa et al. | 250/361 C |
| 5,643,535 A | | 7/1997 | Smethers et al. | |
| 5,653,940 A | * | 8/1997 | Carey et al. | 422/52 |
| 5,714,388 A | * | 2/1998 | Kusnetz | 436/172 |
| 5,798,263 A | * | 8/1998 | Wood et al. | 435/288.7 |
| 5,849,247 A | * | 12/1998 | Uzan et al. | 422/65 |
| 5,980,055 A | * | 11/1999 | Palmer et al. | 362/34 |
| 5,985,671 A | * | 11/1999 | Leistner et al. | 436/49 |
| 6,174,733 B1 | * | 1/2001 | Chen | 436/501 |
| 6,190,617 B1 | * | 2/2001 | Clark et al. | 422/104 |
| 6,375,898 B1 | * | 4/2002 | Ulrich | 422/62 |

* cited by examiner

REACTION WELLS, ASSEMBLY THEREOF, IMMUNOASSAY APPARATUS AND METHOD USING SUCH WELL ASSEMBLIES

This is the National Stage Application of PCT/FR99/02170 filed Sep. 13, 1999.

The present invention relates mainly to reaction vessels, to sets of such vessels for automatic apparatuses for immunological assay, to automatic apparatuses for immunological assay implementing such sets of vessels, and to a method implementing sets of such vessels.

BACKGROUND OF THE INVENTION

FR 96/12546, WO 91/107662, and WO 96/14582 disclose automatic apparatuses for immunological assay essentially comprising means for supporting, guiding, and stepwise displacement of reaction vessels along a path having a predetermined number of positions, a turntable supporting samples to be analyzed, a turntable supporting reagents, means for taking determined quantities of samples and of reagents, and for injecting said taken quantities into the reaction vessels, means for washing the vessels, means for optically reading the results of the assays, and a controlling computer system enabling preprogrammed assay cycles to be performed corresponding to single-reagent or two-reagent assays, said known apparatuses operating at a rate of about 120 assays per hour to 360 assays per hour for the second apparatus.

The apparatus described in international application WO 96/14582 also differs in that it is designed to operate with reaction modules which are parts molded out of transparent plastics material and comprise a plurality of reaction vessels in alignment that are secured to one another, said reaction modules being mass-produced at a very low cost price, thus making it possible to discard them after a single use. Furthermore, such reaction modules are suitable for stacking, thus making them easier to package and also making it easier to stack them in automatic feed means of the apparatus.

FR 96/12546 proposes apparatus of the above-specified type, comprising means for supporting, guiding, and stepwise displacement of sets of reaction vessels along a path comprising a predetermined number of positions, means for supporting samples to be analyzed, means for supporting reagents, means for taking determined quantities of samples and of reagents, and for injecting the taken quantities into the reaction vessels, together with means for washing the vessels, means for reading the results, and means for feeding sets of reaction vessels and for ejecting sets of used vessels, wherein the path of the sets of reaction vessels is rectangular in shape and has two long sides defined by parallel rectilinear support and guide rails for the sets of vessels, and two short sides defined by means for displacing the sets of vessels transversely over three positions comprising two end positions on the long sides of the path and an intermediate position which constitutes the position for ejecting a set of used vessels and the position for feeding a set of new vessels.

Those apparatuses use color-measuring means for reading results through the light-transparent walls of the vessels.

Automatic apparatuses are also known for performing immunological assay, which apparatuses are provided with means for reading the luminescence of the reaction mixture. The apparatuses of known types comprise a dark chamber fitted with light-measuring means for measuring brightness, means for transferring reaction mixtures from a vessel into the dark chamber, means for washing the dark chamber and transfer means, and means for decontaminating the dark chamber and transfer means. As a result, such automatic immunological assay apparatuses are extremely complex and present a cost price that is high.

OBJECTS AND SUMMARY OF THE INVENTION

Consequently, an object of the present invention is to provide immunological assay apparatus that is simple, having means for detecting the luminescence of the reaction mixture.

Another object of the present invention is to provide apparatus that is extremely reliable, always providing results that are accurate and relevant.

It is also an object of the present invention to provide such an apparatus that is capable of operating at high rates of throughput.

It is also an object of the present invention to provide an apparatus that presents a cost price that is moderate.

According to the present invention, these objects are achieved by implementing photometric detection of the luminescence of a reaction mixture in a reaction vessel, the apparatus and/or the vessel providing light-proofing so as to prevent external light entering and falsifying the measurement. Advantageously, the sets of vessels in accordance with the present invention are made out of a material that is opaque.

Preferably, the light-tightness of each assembly constituted by the photometric detection device associated with a vessel filled with reaction mixture is tested.

The invention mainly provides a reaction vessel for automatic apparatus for immunological assay, the vessel comprising walls in the form of a vessel for receiving a sample to be tested, a test reagent, and a substrate coupled with a chemiluminescent substance, and also a filling opening, wherein the walls are proof against any light emitted by the chemiluminescent substance, apart from a window for reading the intensity of any light emitted by the reaction mixture formed by the sample to be tested, the reagent, and the substrate.

The invention also provides a vessel wherein the read window corresponds to the filler opening of the vessel.

The invention also provides a vessel wherein the read window is surrounded by a substantially plane zone against which a light-proof shoe is pressed.

The invention also provides a plurality of vessels according to any preceding claim.

The invention also provides automatic apparatus for immunological assay, comprising means for supporting, guiding, and stepwise displacement of a reaction vessel or sets of reaction vessels along a path comprising a predetermined number of positions, means for supporting samples to be analyzed, means for supporting reagents, and means for taking determined quantities of samples and of reagents and for injecting the quantities taken into the reaction vessels, together with means for washing the vessels, means for reading the results, and means for feeding sets of reaction vessels and for ejecting sets of used vessels, the apparatus including means for forming a temporary dark chamber that is proof against external light, said dark chamber having photometric means for measuring the intensity of light and a vessel or a vessel from a set of vessels.

The invention also provides apparatus including an opaque shoe for pressing in light-proof manner around a read window of a reaction vessel provided with a central opening for passing light between the vessel and photometric means.

The invention also provides apparatus including a plate for receiving the washing means and the photometric means.

The invention also provides apparatus wherein the photometric means include moving equipment for pressing the shoe against the read window of the reaction vessel.

The invention also provides apparatus including a shutter for optically isolating a photoelectric detector, in particular a photomultiplier, and means for measuring the electrical values delivered by the photoelectric detector while it is immersed in the dark, the shutter being closed.

The invention also provides apparatus wherein movement of the moving equipment serves to close or open the shutter.

The invention also provides apparatus including a light source for illuminating, on command, the outside of the dark chamber formed temporarily by the walls of the vessel and the photometric means so as to enable the dark chamber to be tested for light-tightness, the immunological test being rejected if the photometric means detect light emitted by the light-tightness testing source.

The invention also provides apparatus performing a light-tightness test for each reaction vessel subjected to an immunological test.

The invention also provides an automatic method of performing immunological assay, the method comprising a step of detecting the light, if any, emitted by a substrate coupled with a luminescent chemical substance in the presence of a reagent and a sample to be tested, the method including a step of measuring: the light intensity present inside a reaction vessel.

The invention also provides a method wherein a temporary dark chamber is formed with a reaction vessel having an opaque wall and with photometric means.

BRIEF DESCRIPTION OF THE DRAWINGS

The invention will be better understood from the following description and the accompanying figures given as non-limiting examples and in which.

MORE DETAILED DESCRIPTION

In FIGS. 1 to 6 the same references are used to designate the same elements.

Figure 1:
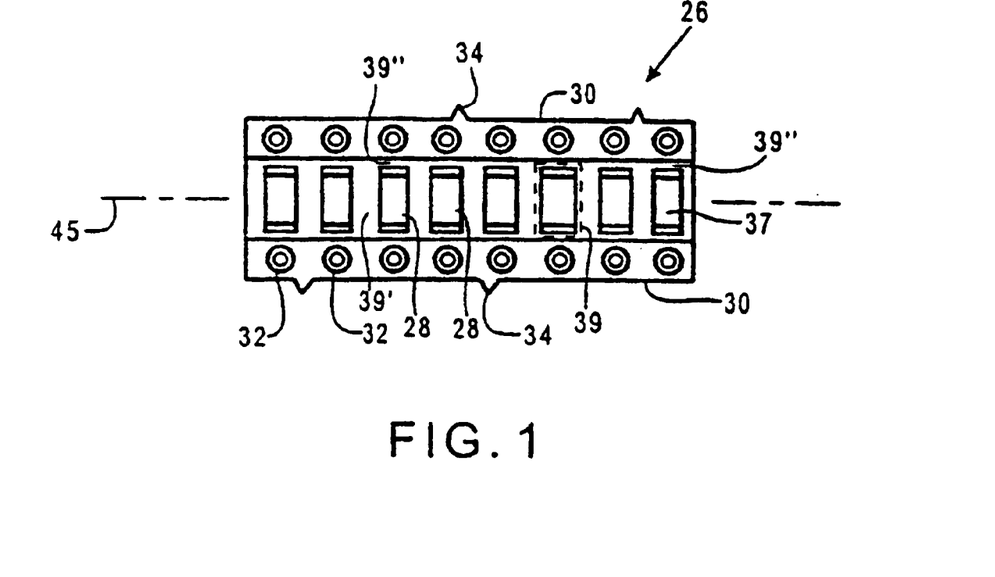
FIG. 1 is a plan view of the preferred set of vessels of the present invention.
Figure 2:
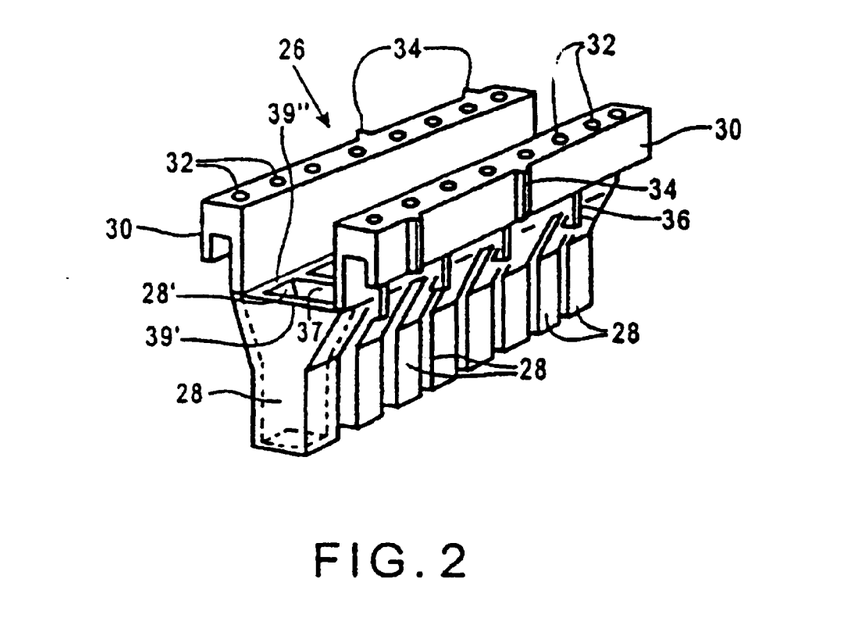
FIG. 2 is a perspective view of: the FIG. 1 set.

In FIGS. 1 and 2, there can be seen the preferred embodiment of a set 26 of reaction vessels 28.

The sets 26 of reaction vessels 28 are made as one-piece moldings of opaque plastics material, in particular of filled polystyrene, each set comprising eight reaction vessels 28 in alignment on a longitudinal axis 45 of the assembly 26 and connected to one another, each set having two L-shaped longitudinal rims 30 extending higher than the open top ends of the vessels 28.

Each longitudinal rim 30 includes, in register with each vessel 28, a frustoconical orifice 32 for use in accurately positioning the set 26 in certain stations of the apparatus of the invention, and each of the outer side faces of the rims 30 has a pair of vertical ribs 34 for co-operating with means for driving the sets 26.

As already described in international application WO 96/14582, the vessels 28 are segments of rectangular-section tube closed at their bottom ends and flaring at their top ends, thereby enabling sets 26 to be stacked vertically while being partially received in one another, with the bottom portion of the vessels 28 in one set 26 penetrating into the flared top ends of the vessels 28 of an underlying set of reaction vessels. This engagement is made easier by the fact that the inside faces of the longitudinal rims 30 diverge slightly apart from each other in an upward direction starting from the open top ends of the vessels 28.

Vertical ribs 36 are formed on the flanks of the enlarged top ends of the vessels 28 and extend a short distance downwards, the bottom ends of the ribs 36 being designed to come into abutment against the top faces of the rims 30 of an underlying set 26 in a vertical stack of sets of reaction vessels.

In addition to being made of opaque material, the sets 26 of vessels in accordance with the present invention differ from those of FR 96/12546 and WO 96/14582 in that each opening 37 of a vessel 28 is surrounded by a substantially plane rim 39 against which an opaque shoe 41 can be pressed (FIGS. 4 to 6), so as to prevent external light from penetrating into a photometric measuring device 43.

The rim 39 is advantageously constituted firstly by a space 39' between vessels and secondly by two margins 39" situated between the walls 30' of the rim 30 and the longitudinal walls 28' of the top portions of the vessels 28.

Naturally, the present invention is not limited in any way to the shape or the material used for the sets 26 of reaction vessels 28.

In a variant, it is possible to use vessels or sets of vessels that are suitable for other kinds of automatic apparatuses for performing immunological assay or to use vessels made using a transparent material that is covered in an opaque layer, e.g. a layer of metallization. Similarly, with a vessel 28 of the present invention it is possible to envisage performing photometric measurement of the luminescence of the reaction mixture through a wall thereof that is not entirely opaque, providing the luminescence coming from a given vessel can be completely isolated from luminescence coming from any adjacent vessel.

For example, it is possible to envisage providing transparent read windows or incorporating a light guide, e.g. in the form of a short optical fiber in the bottom or the side walls parallel to a vertical plane including the longitudinal axis 45 of the set 26. Under such circumstances, the photometric detector means comprise means for isolating the cell being read, such as masks or a shoe analogous to the shoe 41, for example.

Figure 3:
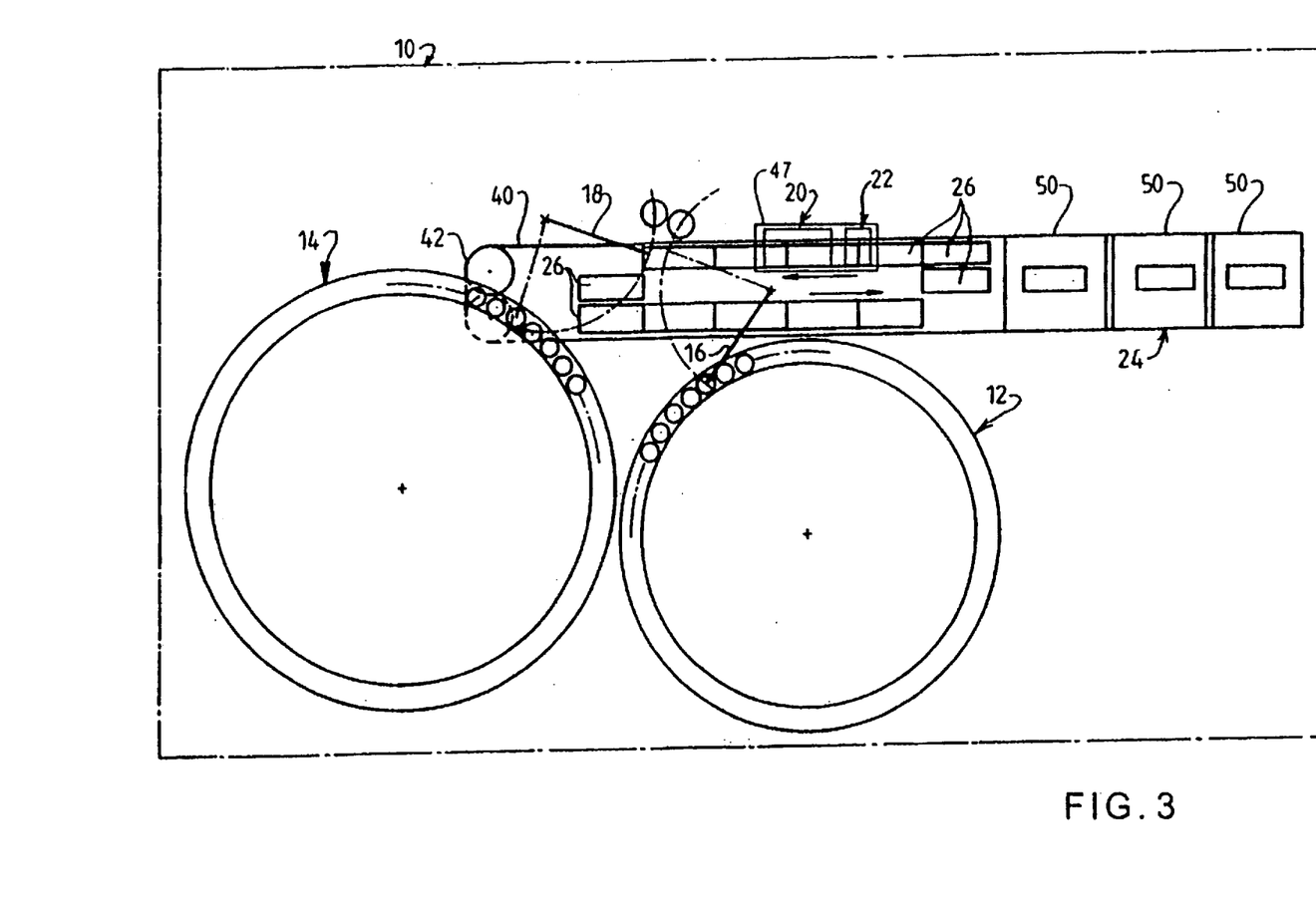
FIG. 3 is a diagrammatic plan view of a preferred embodiment of apparatus of the present invention.

The apparatus of the invention whose general structure is shown very diagrammatically in FIG. 3, comprises a frame 10 having mounted thereon both a turntable 12 for supporting samples to be analyzed and a turntable 14 for supporting assay reagents, together with means 16, 18 for taking determined quantities of samples and of reagents respectively and for depositing said taken quantities in a reaction vessel, said means being of the same type as those described in international application WO 96/14582 and FR 96/12546, the contents of which are incorporated herein by reference.

The reagents used are of the magnetic bead type and the apparatus of the invention comprises means 20 for washing or rinsing such magnetic beads, which means are of the same type as those already described in the above-specified applications and have vertically-displaceable needles for sucking up and injecting liquid, together with permanent magnets located on either, side of the path of the reaction vessels 28 so as to attract by magnetic attraction the magnetic beads carrying the reagents and fix them temporarily on the walls of the reaction vessels. The means 20 also have a needle for depositing a chemiluminescent substrate in the reaction vessels 28, located immediately downstream from the needles for injecting and sucking up washing liquid.

Photometric means 22 for optical reading purposes comprise means 43 for measuring light intensity at the wavelengths of the luminescence of the substrate used. By way of example, a substrate is used containing a disodium salt of 4-methyoxy-4-(3-phosphonatephenyl)spiro[1,2-dioxethane-3,2'-amandane] and sold by LUMIGENE under the reference lumi-Pho 530® which emits in the visible light range with an emission peak corresponding substantially to 530 nm. Under such circumstances, a visible light detector is used whose passband may optionally be narrowed by using a filter that passes only those frequencies that are likely to be emitted. Although using solid state detectors, and in particular semiconductor detectors does not go beyond the ambit of the present invention, the preferred embodiment of the apparatus of the invention uses a photomultiplier tube. The preferred embodiment uses a photomultiplier as sold by HAMAMATSU under the reference H 7155-20.

This type of tube presents the advantage of being able to work at ambient temperature thus making it possible in the preferred embodiment of the invention to provide a machine that does not have any cryostats. Nevertheless, prior to each measurement of the luminescence of a reaction mixture, the apparatus of the invention advantageously performs a measurement in the absence of any light, in the dark, so as to calibrate the reading, in particular the electric voltage, that corresponds to complete darkness. This improves the reliability and the repeatability of measurements, particularly when the volume in which the sets 26 travel is thermostated at 37° C., for example, in order to favor incubation of the reaction mixture.

The output from the photomultiplier 43 is connected via interface and matching means to a computer for monitoring the machine, making use of the results, and/or managing them. For example, the output from the photomultiplier is connected via analog matching means, in particular of the type comprising amplifiers or frequency matching means, to an analog-digital converter whose output is connected to an acquisition, metering, and control card installed in a microcomputer, e.g. of the PC type (not shown).

Figure 4:
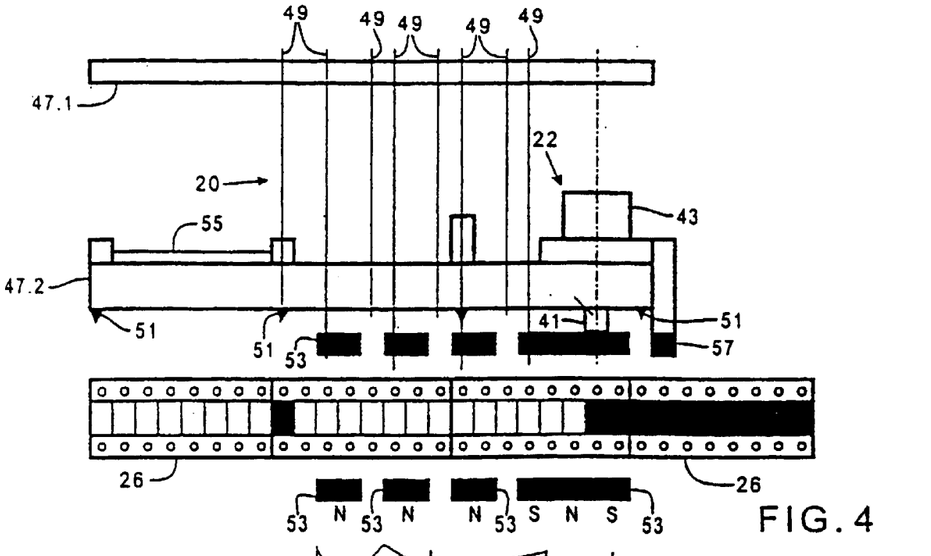
FIG. 4 is a diagrammatic elevation view of a washing and detection device for the apparatus of FIG. 3, with sets of vessels being shown in plan view and on the same scale.

In the advantageous embodiment shown in FIGS. 3 and 4, a common plate 47, e.g. comprising a top plate 47.1 and a bottom plate 47.2 (FIG. 4) carries the washing head 20 and the photometric means 22.

In FIG. 4, the needles for injecting or taking samples are given references 49, while the indexing studs that penetrate into the openings 32 are given the reference 51. Advantageously, the first two indexing studs 51 are united by a spring 55.

The sets 26 of vessels 28 together with magnets 53 oriented in the north-south or the south-north direction are shown in a plane in FIG. 4 so as to give the scale of the plate 47 that has the means 20 and 22.

The apparatus of the invention also has means for displacing the sets of reaction vessels along a path of rectangular shape, with automatic feed means 24 being located at one end thereof to feed it with sets of reaction vessels and also for ejecting such vessels.

Advantageously, the apparatus of the present invention has external bodywork and internal caps of material that is opaque or partially opaque so as to restrict the amount of light that can reach the read window of the photometric means 22.

Advantageously, the apparatus of the present invention has a light source 57, e.g. a light-emitting diode (LED), for verifying the optical isolation of the measurement cavity as formed by the vessel being measured in association with the photometric means 22.

Figure 5:
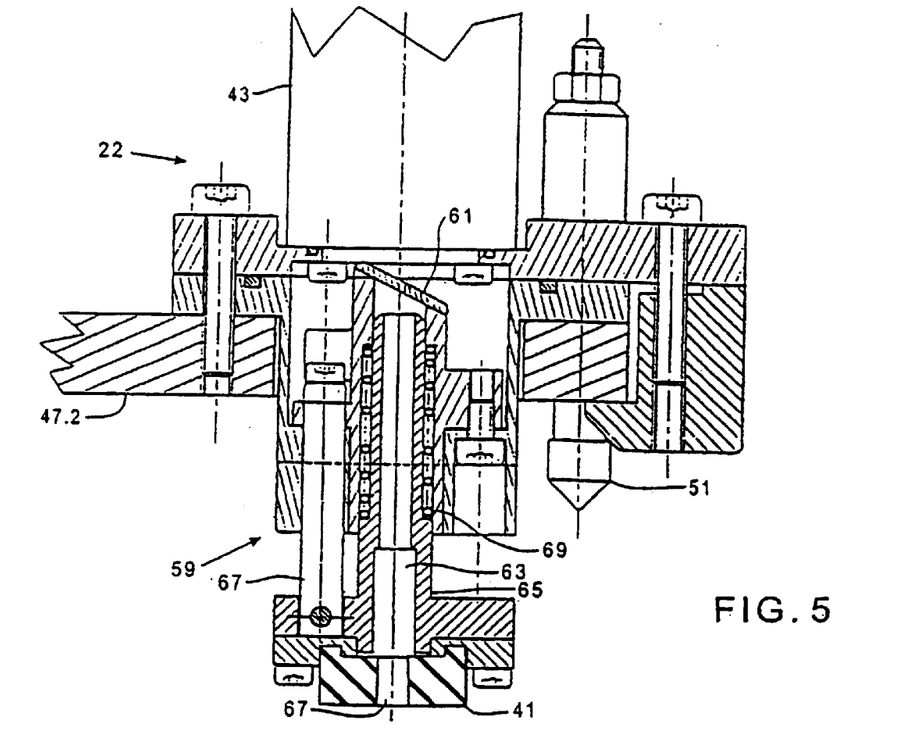
FIG. 5 is a vertical section view of a photometric measuring device implemented in the apparatus of the present invention and shown in a rest condition or a condition for calibrating the measured photometric value for darkness.
Figure 6:
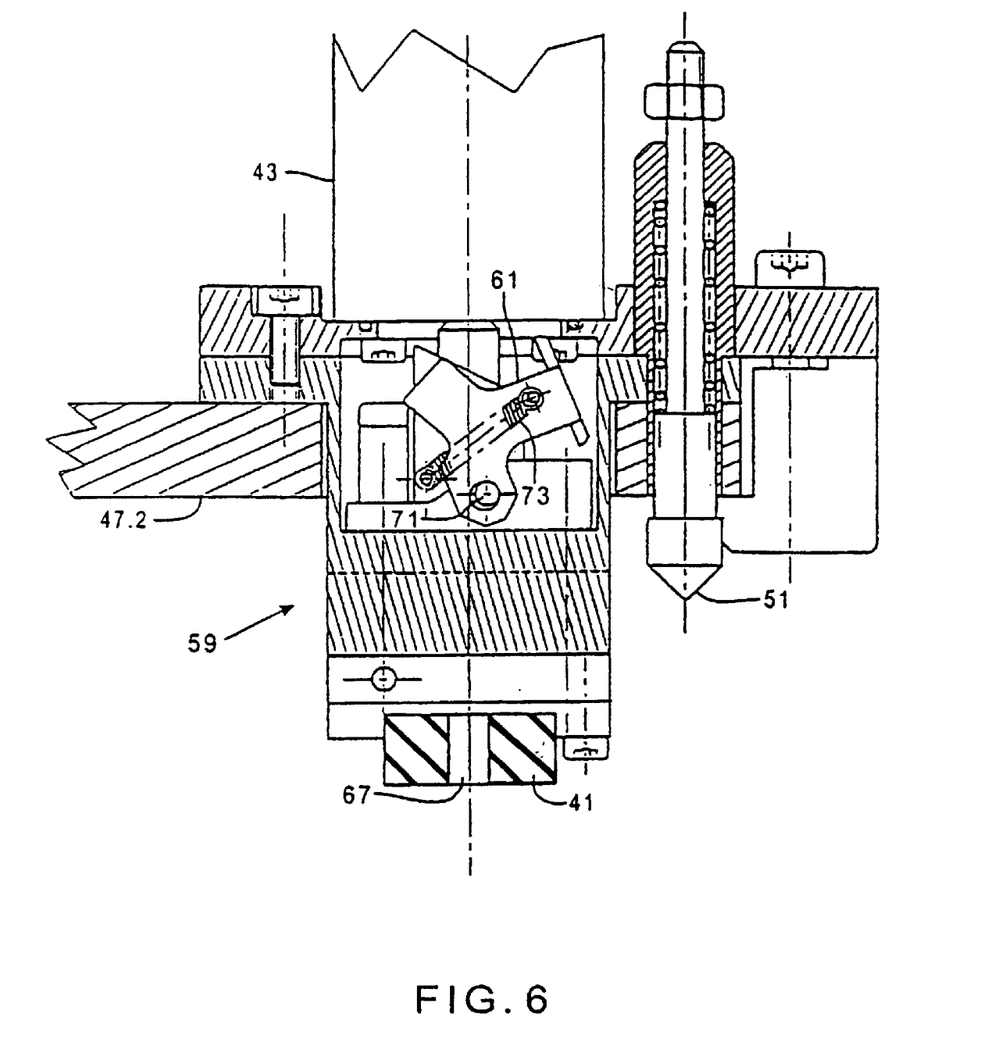
FIG. 6 is a view of the FIG. 5 device in vertical section on a plane orthogonal to the plane of FIG. 5.

In the advantageous embodiment shown, in particular in FIGS. 5 and 6, the photometric mean's 22 comprise the photomultiplier 43 which is fixed relative to the bottom plate 47.2 and moving equipment 59. By way of example, the moving equipment comprises a shutter 61, and a light guide 63 housed in an opaque rigid tubular duct 65 that opens out via an opening 67 in the opaque shoe 41. A rail 67 provides guidance between a low position as shown in FIG. 5 in which the shutter 61 optically isolates the photomultiplier 43 from the light guide 63 and a high position as shown in FIG. 6 in which the shutter 61 is retracted so as to allow communication between the light guide 63 and the photomultiplier 43.

Return means 69, e.g. a helical spring surrounding the rigid tubular duct 65, ensure that the moving equipment 59 returns to the low position shown in FIG. 5. In the advantageous embodiment shown, the shutter 61 is a rotary shutter that is rotatable about an axis of rotation 71 and that has return means, e.g. a helical spring 73 operating in traction for returning it towards the closed position. In the non-limiting example shown, the shutter 61 closes the end of the light guide 63 when the moving equipment 59 is in its low position as shown in FIG. 5, and moves out of the way when the moving equipment 59 is in its high position as shown in FIG. 6.

Naturally, implementing other types of shutter, in particular linear shutters, curtain shutters, or shutters that mask an inlet window to the photomultiplier 43, or even implementing photometric means 22 without any shutter, would not go beyond the ambit of the present invention.

The apparatus of the present invention operates as follows:

The apparatus 10 is loaded firstly with reagents and the substrate, and secondly with the samples (serum) to be tested.

During a first revolution lasting 15 minutes, the vessels 28 of the sets 26 receive from the device 16 the samples to be tested. The sets 26 are driven by the belt 40.

During a second revolution that lasts 15 minutes, the vessels 28 receive the reagents from the device 18.

During a third regulation that lasts 15 minutes, the means 20 wash the magnetic balls and the luminescent substrate is inserted.

During the following revolution (lasting 15 minutes), the result of the test is revealed and then read. Advantageously, to read each vessel 28, the dark level is initially calibrated, i.e. the voltage available at the outlet from the photomultiplier 43 is read while the shutter 61 is closed (low position shown in FIG. 5); then an actuator (not shown) presses the moving equipment 59 against the inlet 37 of a vessel 28. More precisely, the shoe 41 is pressed against the margin 39 of the vessel 28 to be read. The positioning stud 51 ensures accurate positioning with the opening 67 of the shoe 41 being superposed on the inlet 37 of the vessel 28.

In a first embodiment, the set 26 of vessels 28 rises and lifts the moving equipment. In the preferred embodiment, an actuator lowers the lower plate 47.2, thereby causing the moving equipment 59 to rise relative to the plate 47.

The movement of the moving equipment 59 causes the shutter to open and enables the luminescence present in the vessel 28 to be measured.

The moving equipment 59 moves down relative to the plate 47.2 (as shown in FIG. 5), and the light source 57 is switched on, after which a new measurement is performed to verify the light-tightness of the temporary dark chamber formed by the photometric assembly 22 and the vessel 28 under measurement. If the luminescence value obtained during the light-tightness measurement is greater than the value obtained during the measurement proper, it is assumed that the result of the measurement is not reliable. The result of the test is rejected, and advantageously the test is repeated using the same reaction mixture again with the same sample and the same reagent as deposited in a new vessel 28.

Naturally, testing for light-tightness can be performed prior to measuring luminescence without thereby going beyond the ambit of the present invention.

Similarly, measuring the voltage level at the output from the photomultiplier 43 while the shutter 61 is closed can be performed periodically, but not necessarily for all of the measurements.

The present invention is particularly applicable to detecting the presence of a chemical or biological substance in a sample.

The present invention applies mainly to medical analysis and research.

What is claimed is:

1. An automated apparatus for immunological assay, the apparatus comprising:

means for supporting, guiding, and displacing a plurality of reaction vessels along a path having a predetermined number of positions, means for supporting samples to be analyzed, means for supporting reagents, means for taking determined quantities of samples and of reagents and for injecting the quantities taken into each of the reaction vessels, means for washing each of the reaction vessels, means for reading results, means for feeding the plurality of reaction vessels and for ejecting the plurality of reaction vessels, means for forming a temporary dark chamber with each reaction vessel, the temporary dark chamber being proof against external light, photometric means for measuring an intensity of light, wherein each reaction vessel includes walls for receiving a sample to be tested, a test reagent, and a substrate coupled with a chemiluminescent substance, each reaction vessel further includes a filling opening, wherein the walls are proof against any light emitted by the chemiluminescent substance, apart from a window for reading the intensity of any light emitted by a reaction mixture formed by the sample to be tested, the reagent, and the substrate, and wherein the window corresponds to the filling opening of each reaction vessel and wherein the window is surrounded by a substantially planar zone against which a light-proof shoe is pressed, and a light source for illuminating, on command, outside of a dark chamber, wherein the photometric means is operable to test the dark chamber for light-tightness, the immunological assay being rejected if the photometric means detects light emitted by the light source.

2. The apparatus to claim 1, including an opaque shoe for pressing in light-proof manner around the window of the vessel provided with the filling opening for passing light between the vessel and the photometric means.

3. The apparatus according to claim 1, including a plate for receiving the washing means and the photometric means.

4. The apparatus according to claim 1, wherein the photometric means includes a moving equipment for pressing the shoe against the window of the vessel.

5. The apparatus according to claim 1, including a shutter for optically isolating a photoelectric detector and means for measuring electrical values delivered by the photoelectric detector while it is immersed in the dark, wherein the shutter is closed when the photoelectric detector is immersed in the dark.

6. The apparatus to claim 5, further includes a moving equipment, wherein movement of moving equipment serves to close or open the shutter.

7. The apparatus to claim 5, wherein the photoelectric detector is a photomultiplier.

8. A reaction vessel assembly for an automatic chemiluminescence measuring apparatus for immunological assay which includes a photometric device, the assembly comprising:

a vessel comprising walls for receiving a sample to be tested, a test reagent, and a substrate coupled with a chemiluminescent substance, and a filling opening, wherein the walls are proof against any light emitted by the chemiluminescent substance, and the filling opening corresponds to a window for reading an intensity of any light emitted by a reaction mixture formed by the sample to be tested, the reagent, and the substrate, and wherein the filling opening is completely surrounded by a planar rim; and a light-proof shoe that is proof against external light and that is directly pressed against the planar rim to form a temporary dark chamber, the shoe being provided with a central opening for passing light between the vessel and the photometric device.

9. An automated chemiluminescent apparatus for immunological assay, the apparatus comprising:

means for supporting, guiding, and displacing a plurality of reaction vessels along a path having a predetermined number of positions, means for supporting samples to be analyzed, means for supporting reagents, means for taking determined quantities of samples and of reagents and for injecting the quantities taken into each of the reaction vessels, means for washing each of the reaction vessels, means for reading a result, means for feeding the plurality of reaction vessels and for ejecting the plurality of reaction vessels, means for forming a temporary dark chamber with each reaction vessel, the temporary dark chamber being proof against external light, the dark chamber having photometric means for measuring an intensity of light, wherein each reaction vessel includes walls for receiving a sample to be tested, a test reagent, and a substrate coupled with a chemiluminescent substance, each reaction vessel further includes a filling opening, wherein the walls are proof against any light emitted by the chemiluminescent substance, and the filling opening corresponds to a window for reading the intensity of any light emitted by a reaction mixture formed by a sample to be tested, the reagent, and the substrate, wherein the filling opening is completely surrounded by a planar rim, a light proof shoe provided with a central opening for passing light between each reaction vessel and the photometric means and being directly pressed against the planar rim, and a light source positioned external to the dark chamber and operable to illuminate, the photometric means operable to detect the light.

10. The apparatus according to claim 9, including plate for receiving the washing means and the photometric means.

11. The apparatus according to claim 9, wherein the photometric means includes a moving equipment for pressing the shoe against the window of the vessel.

12. The apparatus according to claim 9, including a shutter for optically isolating a photoelectric detector and means for measuring electrical values delivered by the photoelectric detector while it is immersed in the dark, wherein the shutter is closed when the photoelectric detector is immersed in the dark.

13. A method for performing immunological assays that detects light emitted by a reaction mixture consisting of a sample, a reagent and a chemiluminescent substance, said method being performed with an automated chemiluminescent apparatus as set forth in claim 9, said method comprising:

combining a sample and a reagent in a chamber of the reaction vessel having a filling opening;

adding a chemiluminescent substance to the chamber;

pressing a detector directly against the filling opening;

measuring the light emitted from the chamber when the detector is pressed against the filling opening to provide a first reading;

illuminating a light source external to the chamber;

measuring the light emitted from the chamber with the light source illuminating to provide a second reading; and comparing the first reading and the second reading to determine the light-tightness of the chamber.

* * * * *